United States Patent
Boss et al.

(10) Patent No.: US 9,389,213 B2
(45) Date of Patent: Jul. 12, 2016

(54) TABLET TEST STATION

(71) Applicant: PHARMATRON AG, Thun (CH)

(72) Inventors: Thomas Boss, Uetendorf (CH); Holger Herrmann, Thun (CH)

(73) Assignee: PHARMATRON AG, Thun (CH)

( * ) Notice: Subject to any disclaimer, the term of this patent is extended or adjusted under 35 U.S.C. 154(b) by 16 days.

(21) Appl. No.: 14/344,066

(22) PCT Filed: Oct. 19, 2012

(86) PCT No.: PCT/IB2012/055740
§ 371 (c)(1),
(2) Date: Apr. 25, 2014

(87) PCT Pub. No.: WO2013/061226
PCT Pub. Date: May 2, 2013

(65) Prior Publication Data
US 2015/0040678 A1    Feb. 12, 2015

Related U.S. Application Data

(60) Provisional application No. 61/550,975, filed on Oct. 25, 2011.

(30) Foreign Application Priority Data

Oct. 25, 2011  (EP) ...................................... 11186472

(51) Int. Cl.
*G01L 1/24*    (2006.01)
*G01N 33/15*   (2006.01)
(Continued)

(52) U.S. Cl.
CPC .................. *G01N 33/15* (2013.01); *G01N 1/00* (2013.01); *G01N 3/40* (2013.01); *G01N 35/00* (2013.01); *G01N 2203/0087* (2013.01)

(58) Field of Classification Search
CPC ......... G01N 33/15; G01N 3/08; G01B 11/16; G01B 11/20; G01B 5/30
USPC .................................... 73/800, 788, 762, 760
See application file for complete search history.

(56) References Cited

U.S. PATENT DOCUMENTS 1,857,808 A    5/1932    Diederichs
4,219,986 A    9/1980    Osterhaus
(Continued)

FOREIGN PATENT DOCUMENTS

CA    2428801 A1    11/2003
CA    2526758 A1    5/2006
(Continued)

OTHER PUBLICATIONS

International Search Report and International Preliminary Report on Patentability, dated Mar. 1, 2013, from parent PCT/IB2012/055740; in English.
(Continued)

*Primary Examiner* — Lisa Caputo
*Assistant Examiner* — Nigel Plumb
(74) *Attorney, Agent, or Firm* — George Kapsalas; Patentbuero Paul Rosenich AG

(57) ABSTRACT

The invention relates to a tablet test station, including at least one receptacle for the transfer of tablets from an outlet of a feed device and at least one test means for inspecting, testing and/or measuring the tablets. A lifting device (20) is provided for moving the receptacle (15) relative to the feed device (13).

19 Claims, 3 Drawing Sheets

Figure 1:
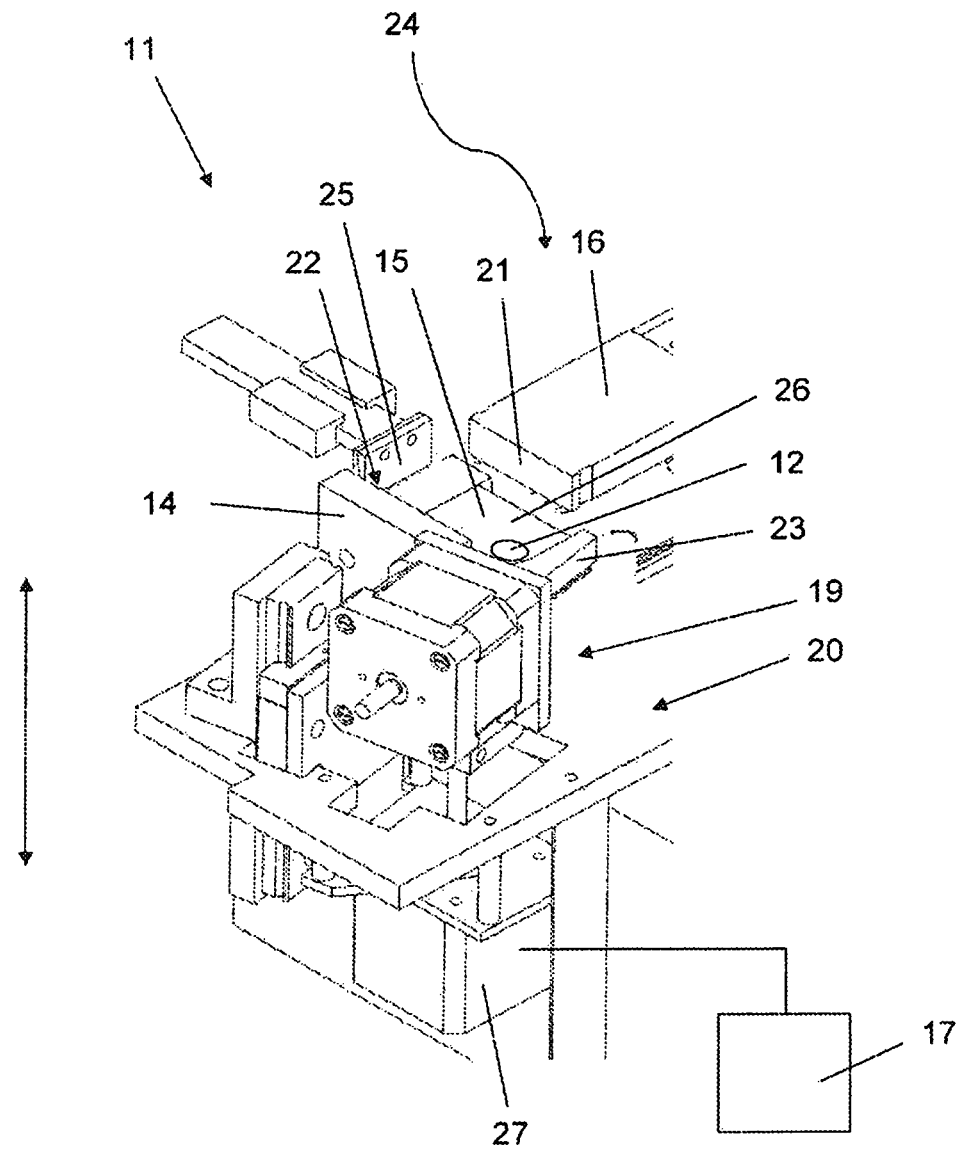

(51) Int. Cl.
*G01N 3/40* (2006.01)
*G01N 1/00* (2006.01)
*G01N 35/00* (2006.01)

(56) References Cited

U.S. PATENT DOCUMENTS

| | | | |
|---|---|---|---|
| 4,393,717 A * | 7/1983 | Mason | G01B 7/06 |
| | | | 209/558 |
| 4,434,887 A | 3/1984 | Yager | |
| 4,472,960 A * | 9/1984 | Motoyama | G01N 33/15 |
| | | | 33/501 |
| 4,542,646 A | 9/1985 | Smith et al. | |
| 4,546,901 A | 10/1985 | Buttarazzi | |
| 4,660,713 A | 4/1987 | Kaminski | |
| 4,784,275 A | 11/1988 | Fridge | |
| 4,907,790 A | 3/1990 | Sugiura et al. | |
| 4,930,289 A | 6/1990 | Fransson et al. | |
| 5,012,913 A | 5/1991 | Kraemer | |
| 5,190,162 A | 3/1993 | Hartlepp | |
| 5,240,118 A | 8/1993 | Mayer | |
| 5,466,290 A | 11/1995 | Berta | |
| 5,503,673 A | 4/1996 | Berta | |
| 5,522,512 A | 6/1996 | Archer et al. | |
| 5,555,768 A * | 9/1996 | Shaffer | G01B 5/0002 |
| | | | 73/821 |
| 5,638,417 A * | 6/1997 | Boyer | A61J 7/02 |
| | | | 377/6 |
| 5,679,406 A | 10/1997 | Berta | |
| 5,971,038 A * | 10/1999 | Fiedler | G01G 17/00 |
| | | | 141/173 |
| 6,237,743 B1 | 5/2001 | Bracher | |
| 6,260,419 B1 * | 7/2001 | Kramer | G01N 33/15 |
| | | | 73/78 |
| 6,820,498 B2 * | 11/2004 | Kalbermatten | G01G 17/00 |
| | | | 73/788 |
| 7,364,103 B2 | 4/2008 | Kraemer et al. | |
| 2003/0209098 A1 | 11/2003 | Kalbermattern | |
| 2004/0144618 A1 | 7/2004 | McDonald et al. | |
| 2005/0103132 A1 * | 5/2005 | Bracher | G01N 3/40 |
| | | | 73/866 |
| 2005/0263537 A1 | 12/2005 | Gerold et al. | |
| 2006/0260413 A1 * | 11/2006 | Kraemer | G01N 3/04 |
| | | | 73/818 |
| 2008/0105516 A1 * | 5/2008 | Richwine | B01L 3/0241 |
| | | | 198/771 |

FOREIGN PATENT DOCUMENTS

| | | |
|---|---|---|
| DE | 8911221 U1 | 11/1989 |
| DE | 4241985 A1 | 6/1994 |
| DE | 19744227 A1 | 11/1998 |
| DE | 102004036777 A1 | 3/2006 |
| DE | 102004059976 A1 | 6/2006 |
| DE | 202008003673 U1 | 5/2008 |
| DE | 102007056244 A1 | 5/2009 |
| DE | 102008035830 A1 | 2/2010 |
| DE | 102010012198 A1 | 9/2011 |
| EP | 0685714 A1 | 12/1995 |
| EP | 1361418 A1 | 11/2003 |
| EP | 1531317 A1 | 5/2005 |
| FR | 2142655 A | 2/1973 |
| FR | 2933079 A1 | 1/2010 |
| GB | 728097 A | 4/1955 |
| GB | 728111 A | 4/1955 |
| GB | 871685 A | 6/1961 |
| GB | 1032417 A | 6/1966 |
| GB | 1288584 A | 9/1972 |
| GB | 2214500 A | 9/1989 |
| JP | S61-084556 A | 4/1986 |
| JP | S61-127519 A | 6/1986 |
| JP | S62-295432 A | 12/1987 |
| JP | H02-099862 A | 4/1990 |
| JP | H02-255149 A | 10/1990 |
| JP | H05-079964 A | 3/1993 |
| JP | H05-079966 A | 3/1993 |
| JP | S63-076863 A | 4/1998 |
| JP | H10-160554 A | 6/1998 |
| JP | 2001-095897 A | 4/2001 |
| JP | 2003-347330 A | 12/2003 |
| WO | 2009/038380 A2 | 3/2009 |
| WO | 2011/035818 A1 | 3/2011 |
| WO | 2013/061223 A3 | 6/2014 |

OTHER PUBLICATIONS

European Search Report of EPO in priority Application No. EP11186472, dated Mar. 20, 2012.

Copending commonly owned U.S. Appl. No. 14/344,063 mentioned at Specification paragraph[0016].

* cited by examiner

TABLET TEST STATION

This application is a 35 U.S.C. 371 national-phase entry of PCT International application no. PCT/IB2012/055740 filed on Oct. 19, 2012 and also claims benefit of priority to prior European application no. EP11186472 filed on Oct. 25, 2011, and also claims priority as a non-provisional of U.S. provisional application Ser. No. 61/550,975 filed on Oct. 25, 2011, and both European application no. EP11186472 and U.S. provisional application Ser. No. 61/550,975, as well as parent PCT International application no. PCT/IB2012/055740, are all incorporated herein by reference in their entireties for all intents and purposes, as if identically set forth in full herein.

The invention relates to tablet test stations, to machines for testing tablets by means of tablet test stations, and to methods for testing tablets in tablet test stations.

In research and industry, such tablet test appliances are used to meet the very high quality requirements, particularly in the pharmaceutical field. These appliances may be operated manually, either semi-automatically or fully automatically. For example, they measure weight, thickness, diameter, length and width, and hardness, that is to say breaking strength and breaking behaviour, of tablets using mechanical, electronic, optical, chemical or acoustic methods. Since tablets are provided in a wide range of forms, optimal and reliable positioning of a tablet relative to measuring apparatus in a respective method poses a great challenge to the developers and users of such tablet test appliances. This is true in particular if different test methods, which require different positionings of the tablet, are carried out on one tablet test station.

Test stations for testing tablets, including a receptacle for transferring tablets from an outlet of a feed device and at least one tester means for inspecting, testing and/or measuring the tablets, are described in the prior art.

A method for measuring the thickness and hardness of test specimens, in particular tablets, and a rotary plate for this purpose are described in EP 1531317A1. In that case, a test station with a rotary plate as a receptacle of tablets is described, these tablets being subjected thereon to a measurement method to establish length and diameter. The tablets are then lifted individually from the rotary plate by a pick-up and are put down in another test station.

This method has a number of drawbacks. There are test stations of different design for different test methods. There are accordingly also different feeds or transfers. Each of these test stations requires space and generates additional costs. Each transfer costs time.

A device for carrying out a hardness test, and a length, width, and height measurement of a test specimen, in particular of a tablet, in a single test station is described in DE 102008035830A1. The device has a base plate as a receptacle for the transfer of the tablet from a feed device, and has means for inspecting, testing and/or measuring the tablet. The test station is shown with a pressure cell, a pressure plate, a stop piece and a laser measurement unit, in which the stop piece, sliding rails connected to a slider, and a spindle for displacing alignment pincers are arranged on the base plate. To this end, alignment pincers are described, which have cavity-like openings with a recess for positioning of the tablet and which have a measuring gap. A table plate displaceable in the direction of the stop piece is provided for the tablet on the base plate. The pressure sensor is connected to the slider and to the pressure plate.

This solution is complex and is not suitable for all designs of tablet test stations or for all types of tablet feed.

The prior art may be summarised in that a different positioning of the tablets in the tablet test station before and/or during the different operation steps is achieved insufficiently or only with considerable effort. If the tablet is not brought into the correct position for each measurement method or test method, often due to its specific shape, the measurement result or test result is inadequate. Each subsequent positioning of the tablet, so as to obtain an optimal test result, delays the course of the process and therefore leads to poorer economic viability of the tablet test station. The testing of unusual tablet shapes is particularly problematic, because such tablets cannot be brought into the necessary position by a universal method.

U.S. Pat. No. 4,393,717A and DE 102010012198A1 each disclose ramps for the tablets, leading from the feed device to the test device. U.S. Pat. No. 4,393,717A further discloses an opening through which the tablets may fall on the ramp.

The drawbacks of these devices include the fact that an exact positioning of the tablet by a ramp is only possible by additional rolls or other devices. Furthermore, the velocity of the transport is not precisely controllable by such embodiments.

The object of the invention is therefore to overcome the aforementioned drawbacks and to provide a tablet test station, which is simpler and more convenient in terms of design and in which tablets of any shape may be positioned in a highly accurate manner and different test methods may be carried out at maximum speed.

In accordance with the invention, a lifting device for moving the receptacle relative to the feed device, for transfer of the tablets therefrom, is provided and is formed in the manner of a lift.

This lifting device is particularly advantageously formed in combination with specifically formed feed devices and/or with a pivotable receptacle for tablets, as described in the Applicant's commonly owned U.S. application Ser. No. 14/344,063 filed as International application no. PCT/IB2012/055735 claiming priority to prior application EP11186470.8 filed on Oct. 25, 2011 and titled "Tablet Testing Device" filed on the same date as the present Application, the entirety of which is incorporated herein by reference, as to all its parts, for all intents and purposes. This commonly owned U.S. application Ser. No. 14/344,063 forms an integral part of the present Application.

The lifting device is associated with economic and technical improvements. It allows adapted-to-the-process, precise positioning, of any conceivable tablet within the shortest time and, in principle, is conceivable with any test method and with any type of automatic feed. In this case, automatic feed is understood to mean any type of feed which is not carried out purely manually. A specific advantage of the invention lies in the fact that the receptacle for the tablet may be moved very close to the outlet of the feed device so that the tablet o be transferred does not fall onto the receptacle in an uncontrolled manner and lie at any point thereon, as in the prior art, but is already positioned for the (preferably first) test method. A further advantage of the invention lies in the fact that the tablet may be positioned as close as possible to the fixed jaw. Time-consuming displacement of the tablet during the subsequent measurement process therefore is not necessary, and the risk of the tablet rotating may be ruled out.

The lifting device advantageously has a motor, which particularly advantageously is controlled by a controller so as to ensure rapid and precise positioning.

In a preferred version the means for inspecting, testing and/or measuring the tablets is formed as a length and/or width and/or thickness measurement device or sensor, which preferably has at least one positioning face for positioning the tablet on the receptacle.

This means for inspecting, testing and/or measuring is particularly preferably an optical sensor arrangement, since this operates quickly and precisely.

Ira a preferred embodiment the means for inspecting, testing and/or measuring is formed as a breaking strength measurement device or sensor and/or as a device for testing breaking behaviour.

In a particularly preferred version, the breaking strength measurement device comprises a breaking device, which has at least one positioning face for positioning the tablet. The employment of at east parts of means for inspecting, testing and/or measuring as positioning faces reduces the number of additionally required positioning faces, for example on the receptacle.

In a preferred embodiment the receptacle has at least one positioning face for positioning the tablet, this face being formed as a deflector in a particularly preferred embodiment. This allows simple and quick positioning of the tablet.

In a preferred embodiment, the receptacle is formed as at least one flap. This can likewise be pivoted for positioning of the tablet for a test method and for discharge of the tablet from the tablet test station.

In a preferred embodiment, with the arrangement of a plurality of means for inspecting, testing and/or measuring the tablets, such means are arranged in a planar arrangement. With this arrangement, the tablet test station is able to carry out the test methods without interruption and therefore at the greatest possible speed.

A tablet test station according to the invention may be advantageously used in a machine for testing tablets, such machine including a plurality of preferably different tablet test stations and/or other apparatuses, such as a feed device.

The preferred method for testing tablets using a tablet test station or using a machine comprising a tablet test station according to the invention comprises the steps of moving the receptacle, for transfer of the tablet, via the lifting device into a position adjacent to the feed device, transferring the tablet from the feed device to the receptacle, and then moving the receptacle into at least one second position to carry out tests. Tests are to be understood in this context to also include inspections and measurements.

The lifting device most advantageously moves the receptacle for transfer of the tablet into a first position so that the distance of the receptacle from the outlet of the feed device is greater than the thickness of the respective tablet o be inspected, but preferably as close as possible. In some cases this first position could even be chosen in a way that the distance of the receptacle from the outlet of the feed device is smaller than the thickness of the respective tablet to be inspected. The feed device is thus able, depending on the design thereof and the form of the tablet, to position the tablet on the receptacle at a predefined point with precise orientation. So as to achieve the best result in this regard, the feed device is provided with outlets which outlets enable defined positioning.

Transfer and the subsequent test method(s) may be carried out with the lifting device in a manner, and in particular at the height within the machine comprising a tablet test station or test station, as provided for originally by design. The lifting device thus constitutes a relatively simple and, compared to a new design of a tablet test station or of an entire machine comprising a tablet e station for optimisation purposes, a cost-effective improvement to the design-induced drawbacks of tablet test devices comprising feed devices, this lifting device in particular also being suitable for retrospective installation in a machine including a tablet test station.

In an advantageous embodiment, the tablet is discharged from the tablet test station upon conclusion of the method, whether it is to be subjected to a further test method or whether it is to be disposed of.

The list of reference labels forms part of the disclosure.

The invention shall be explained in greater detail symbolically and by way of example on the basis of figures.

The drawing figures will be described in succession and comprehensively. In the drawings, like reference signs denote like components.

In the figures:

FIG. 1—shows a schematic view of a first exemplary embodiment according to the invention of a tablet test station, FIGS. 2-5 show an exemplary embodiment according to the invention of a tablet test station during various phases of the method carried out therein.

For simplification, arrangements according to the invention are described in an exemplary machine via a preferred embodiment of a tablet test station which inspects length, width and hardness, that is to say breaking strength and/or covering behaviour, but are in no way limited to this specific tablet test station.

FIG. 1 shows a tablet test station 11 comprising a lifting device 20, the controller 17 of which passes on to the drive, in particular a motor 27 (although another drive means or drive devices, for example a pneumatically operated device would also be conceivable) of the lifting device 20, positions for the receptacle 15, into which it is moved for transfer from the feed device or to carry out a method step during inspection, testing and/or measurement of a tablet and in which it is held during the respective method step.

The receptacle 15 for a tablet 12 is movable in this case, formed as a flap with a positioning face 26 and a deflector 23. It is shown with its separate drive 19, with which it is moved vertically and jointly by the lifting device 20. A breaking device 24 is provided, which includes a fixed breaking jaw 14 and a displaceable breaking jaw 16. The fixed breaking jaw 14 has a positioning face 22. The displaceable breaking jaw 16 has a positioning face 21.

If the lifting device 20 is lowered, as illustrated in this case, the displaceable breaking jaw 16 is displaced over the receptacle 15 in the direction of the fixed breaking jaw 14, both for positioning of the tablet 12 for the measurement method(s) and for a breaking strength test on the tablet 12, or to inspect the breaking behaviour. The positioning face 21 abuts the tablet 12 and, provided the tablet is not already positioned against the fixed breaking jaw, which is generally desired, displaces it until it abuts the positioning face 22 and is oriented at right angles to the fixed breaking jaw 14. A width, length and/or thickness measurement is then taken on the tablet by means of a measurement device 25. The tablet 12 is then brought into a perpendicular position relative to the fixed breaking jaw 14, preferably by at least one pivotal movement of the receptacle 15 or, if the receptacle 15 is formed in two parts, by a pivotal movement of the receptacle faces into a V-position in relation to one another. The breaking strength or breaking behaviour test is then carried out, in which the positioning face 21 of the displaceable breaking jaw presses the tablet 12 against the fixed breaking jaw 14, wherein the tablet may break. The tablet 12 or the broken parts thereof is/are then removed from the tablet test station 11, preferably by pivoting the receptacle 15.

FIGS. 2 to 5 depict different phases of the (above-described) test method, Particular notice is paid to the feed device. In principle, the tablet may be transferred by means of any known feed device. However, the described lifting device is particularly advantageous for feed devices of which the transfer point, that is to say the outlet or the like, for design reasons is distanced relatively far during the feed process from the face which is to receive the tablet for at least the first test method. The greater the distance between the outlet of the feed device and the receptacle for the tablet, the greater the risk that the tablet will fall or slip onto the receptacle in an uncontrolled manner and will thus come to lie at a point which is inconvenient for the subsequent test method. However, a specific pre-orientation of the tablet on the receptacle is mandatory for specific tablet forms to obtain a usable test result.

Figure 2:
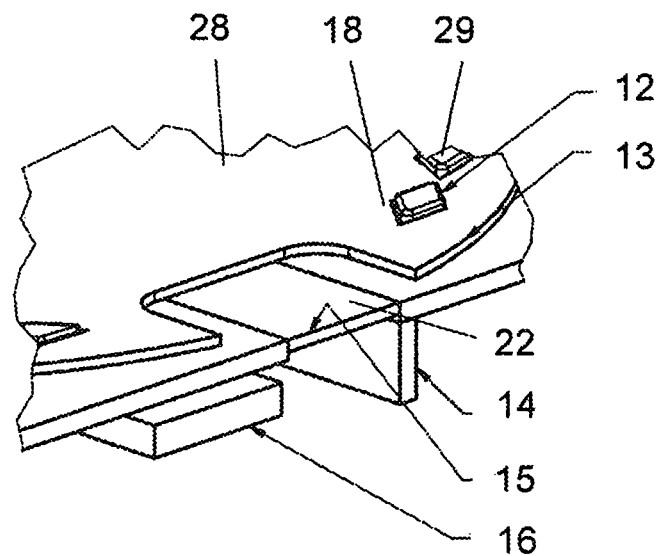

FIG. 2 depicts the transport of a tablet 12 to the receptacle 15 by means of a feed device 13. The feed device 13 is illustrated in a preferred embodiment in the form of a rotary plate 28. However, any other type of preferably automatic feed device is equally conceivable, for example a linear conveyor. The rotary plate 28 is illustrated by way of example in each of FIGS. 2 to 5 with a plurality of rectangular outlets 18, 29, 39, which are formed as recesses. Of course, any other appropriate shape of the outlets 18, 29, 39 is also conceivable. In a preferred embodiment the rotary plate 28 has outlets which are shaped in such a way that they are adapted to put down tablets in the position ideal for the subsequent method. While the feed device 13 conveys the (next) tablet 12 to the receptacle, the lifting device 20 (not shown here) is held at a height which allows the smallest possible spacing of the receptacle 15 from the feed device 13. The displaceable breaking jaw 16 is held at a distance from the fixed breaking jaw 14, which allows the lifting apparatus 20, in a subsequent step, to move the receptacle 15 downwards between two breaking jaws 14 and 16.

Figure 3:
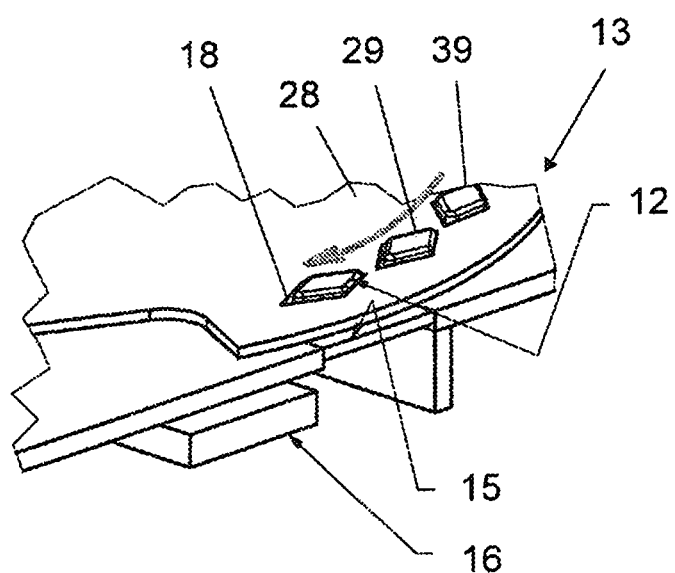

In FIG. 3 the rotary plate 28 is moved in such a way that the outlet 18 of the rotary plate 28 lies above the receptacle 15 so that the tablet 12 is put down in the position predefined therefor. The lifting device 20 and breaking jaw 16 are still located in the same position as in FIG. 2.

Figure 4:
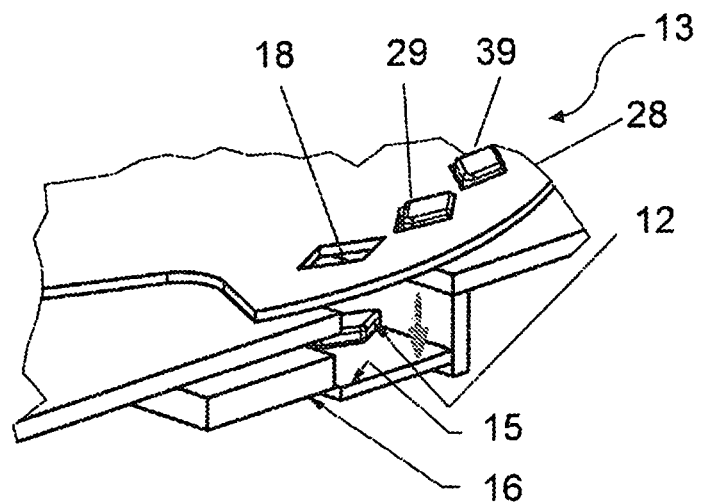

In FIG. 4, the tablet 12 is now put down on the receptacle 15 and the outlet 18 is again seen as free. The lifting device 20 has moved the receptacle 15 into a position where the distance of the receptacle 15 from the outlet 18 of the feed device 13 is greater than the thickness of the tablet 12. This movement places the receptacle 15 so far downwards relative to the feed device 13 that a test method, for example a method for establishing length, width or thickness, is carried out within the tablet test station 11 at the design-induced height of the measurement apparatuses and the tablet 12 may be positioned accordingly.

Figure 5:
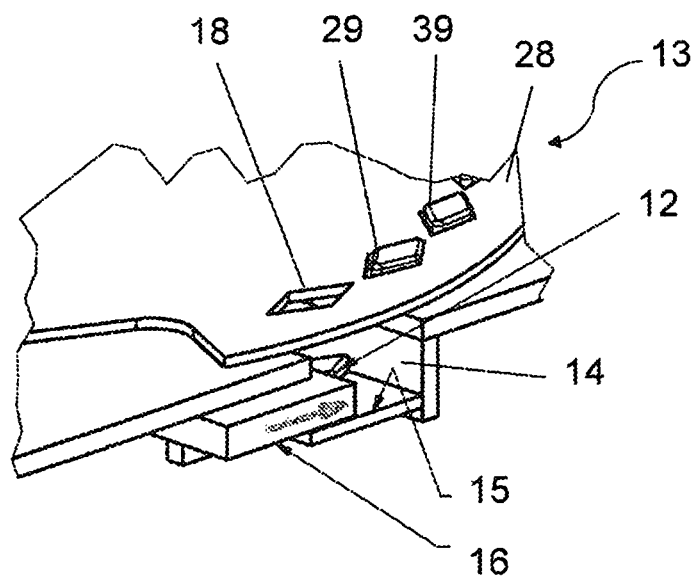

FIG. 5 depicts how the displaceable breaking jaw 16 has displaced the tablet 12 for breaking strength inspection in the direction of the fixed breaking jaw 14 or how the tablet could already be so positioned without displacement. The lifting device 20 holds the receptacle 15 in the same, lower position as shown in FIG. 4. If the tablet 12 has then been discharged from the tablet test station 11, the lifting device 20 again moves upwardly relative to the feed device 13, as described in FIG. 2.

Of course, the individual details described in conjunction with the figures may also be provided in the other embodiments that le within the scope of the patent claims.

LIST OF REFERENCE LABELS 11 tablet test station
12 tablet
13 feed device
14 fixed breaking jaw
15 receptacle for tablets
16 displaceable breaking jaw
17 controller
18 outlet
19 drive for receptacle and for mounting thereof
20 lifting device
21 positioning face of the displaceable breaking jaw
22 positioning face of the fixed breaking jaw
23 deflector
24 breaking device
25 optical measurement device
26 positioning face of the receptacle
27 drive, in particular motor of the lifting device
28 rotary plate
29,30 outlet

What is claimed is:

1. A tablet test station comprising:
a tablet receptacle;
a tablet feeder configured to transfer tablets to said receptacle;
a tablet tester configured to obtain at least one tablet characteristic;
a lift operatively connected to said receptacle to move said receptacle from a first position for transfer of tablets to at least one second position for tablet testing.

2. A tablet test station as claimed in claim 1, further comprising;
a drive motor included in said lift.

3. A tablet test station as claimed in claim 2, further comprising:
a controller operatively connected to said drive motor.

4. A tablet test station as claimed in claim 1, further comprising:
said tablet tester has at least one positioning face configured to position tablets on said receptacle, said tablet tester measuring at least one tablet dimension.

5. A tablet test station as claimed in claim 1, further comprising:
an optical sensor included in said tablet tester.

6. A tablet test station as claimed in claim 1, further comprising:
said tablet tester including a breaking strength measurement device.

7. The tablet test station as claimed in claim 1, further wherein:
said tablet tester measures breaking behavior.

8. A tablet test station as claimed in claim 1, further comprising:
said tablet tester includes a tablet breaker, and said tablet breaker has at least one positioning face configured to position tablets.

9. A tablet test station as claimed in claim 1, further comprising:
said receptacle having at least one positioning face configured to position a tablet.

10. A tablet test station as claimed in claim 9, further comprising:
said positioning face including a deflector.

11. A tablet test station as claimed in claim 1, further comprising:
said receptacle having at least one flap.

12. A tablet test station as claimed in claim 1, further comprising:
a plurality of tablet testers, said plurality of tablet testers being in a planar arrangement.

13. A method for testing tablets comprising steps of:
transferring tablets towards a receptacle location with a tablet feeder;

activating a lift to lift the receptacle into a first position adjacent to the tablet feeder;

transferring a tablet from the tablet feeder to the receptacle;

moving the receptacle into a second position; and, executing at least one test on the tablet.

14. A method for testing tablets as claimed in claim 13 further comprising the steps of: positioning a tablet on the receptacle via at least one positioning face of a tablet tester; and, measuring at least one dimension of a tablet with the tablet tester.

15. A method for testing tablets as claimed in claim 13 further comprising the step of:

measuring a tablet breaking strength with a tablet tester.

16. A method for testing tablets as claimed in claim 13 further comprising the step of:

measuring tablet breaking behavior with a tablet tester.

17. A method for testing tablets as claimed in claim 13 further comprising the step of:

positioning a tablet via at least one positioning face of a tablet breaker.

18. A method for testing tablets as claimed in claim 13 further comprising the step of: positioning a tablet via at least one positioning face of the receptacle.

19. A method for testing tablets as claimed in claim 13 further comprising the step of:

discharging a tablet from the receptacle.

* * * * *